(12) United States Patent
Bergonzelli Degonda et al.

(10) Patent No.: US 10,821,139 B2
(45) Date of Patent: Nov. 3, 2020

(54) METHOD OF USING BIFIDOBACTERIUM LONGUM TO TREAT DEPRESSIVE SYMPTOMS

(71) Applicant: NESTEC S.A., Vevey (CH)

(72) Inventors: Gabriela Bergonzelli Degonda, Bussigny (CH); Tiago Alves Nunes, Bern (CH); Valerie Marquardt, Epalinges (CH); Jeroen Antonius Johannes Schmitt, Moudon (CH)

(73) Assignee: Societe des Produits Nestle S.A., Vevey (CH)

( * ) Notice: Subject to any disclaimer, the term of this patent is extended or adjusted under 35 U.S.C. 154(b) by 110 days.

(21) Appl. No.: 15/754,734

(22) PCT Filed: Aug. 31, 2016

(86) PCT No.: PCT/EP2016/070461
§ 371 (c)(1),
(2) Date: Feb. 23, 2018

(87) PCT Pub. No.: WO2017/037089
PCT Pub. Date: Mar. 9, 2017

(65) Prior Publication Data
US 2018/0250348 A1 Sep. 6, 2018

Related U.S. Application Data

(60) Provisional application No. 62/212,148, filed on Aug. 31, 2015, provisional application No. 62/220,408, (Continued)

(51) Int. Cl.
*A61K 35/745* (2015.01)
*A23L 33/135* (2016.01)
*A61P 25/24* (2006.01)

(52) U.S. Cl.
CPC .......... *A61K 35/745* (2013.01); *A23L 33/135* (2016.08); *A61P 25/24* (2018.01);
(Continued)

(58) Field of Classification Search
CPC ........ A23L 33/135; A23L 33/21; A23L 33/19; A23L 33/40; A23L 29/30; A23L 29/35; A23L 33/10; A23L 33/125; A23L 33/15; A23L 33/16; A23L 5/00; A23L 7/00; A23L 33/12; A23L 33/26; A23L 33/115; A23L 33/17; A23L 33/30; A23L 33/105; A23L 2/66; A23L 2/52; A23L 33/13; A23L 33/165; A23L 33/18; A23L 15/38; A23L 2/38; A23L 2/395; A23L 33/127; A61K 35/745; A61K 2300/00; A61K 35/747; A61K 31/702; A61K 38/018; A61K 35/20; A61K 35/741; A61K 9/0053; A61K 31/202; A61K 38/40; A61K 31/519; A61K 33/26; A61K 31/14; A61K 31/688; A61K 31/685; A61K 33/06; A61K 33/30; A61K 31/7032; A61K 31/714; A61K 33/42; A61K 31/133; A61K 9/0095; A61K 31/715; A61K 31/20; A61K 31/661; A61K 45/00; A61K 33/34; A61K 31/201; A61K 45/06; A61K 31/70; A61K 31/7088; A61K 33/00;
(Continued)

(56) References Cited

U.S. PATENT DOCUMENTS 8,343,482 B2 * 1/2013 Bergonzelli .......... A61K 35/745
424/93.3
8,603,492 B2 * 12/2013 Mercenier ............ A61K 35/744
424/282.1
(Continued)

FOREIGN PATENT DOCUMENTS

| EP | 2110028 | 10/2009 |
| WO | 2007093619 | * 8/2007 |
| WO | 2010060722 | 6/2010 |

OTHER PUBLICATIONS

Guo et al "Irritable Bowel Syndrome Is Positively Related to Metabolic Syndrome: A Population-Based CrossSectional Study" PLOS ONE | www.plosone.org Nov. 1, 2014 | vol. 9 | Issue 11 | e112289. (Year: 2014).*
(Continued)

*Primary Examiner* — Deborah K Ware
(74) *Attorney, Agent, or Firm* — K&L Gates LLP

(57) ABSTRACT

Compositions and methods use *Bifidobacterium longum* NCC3001 (ATCC BAA-999) to treat or prevent a depressive symptom. Prolonged anti-depressive effects can continue after administration of the compositions is ended. Non-limiting examples of a depressive symptom which can be treated or prevented include depressed mood; sadness; anxiety; "empty" feelings; loss of interest or pleasure; irritability; restlessness; changes in appetite or weight; sleep disturbances; lack of or decreased energy; feelings of worthlessness; guilt; helplessness; anger and hostility; difficulty in thinking, concentrating, or making decisions; hopelessness; tiredness; fatigue; memory difficulties; tearfulness; brooding; phobias; excessive worry over physical health; sexual dysfunction; persistent physical symptoms that do not respond to treatment; and combinations thereof. These depressive symptoms can be associated with a depressive state or depressive disorder or can be found subclinically or not associated with these depressive states/disorders (e.g., not part of a syndrome or psychiatric disorder).

2 Claims, 6 Drawing Sheets

Related U.S. Application Data filed on Sep. 18, 2015, provisional application No. 62/236,639, filed on Oct. 2, 2015.

(52) U.S. Cl.
CPC ... *A23V 2002/00* (2013.01); *A23V 2200/3202* (2013.01); *A23V 2200/322* (2013.01); *A23V 2200/3204* (2013.01)

(58) Field of Classification Search
CPC .............. A61K 31/683; A61K 31/7048; A61K 31/716; A61K 38/482; A61K 35/74; A61K 35/742; A61K 35/744; A61K 31/397; A61K 31/424; A61K 31/427; A61K 31/43; A61K 31/431; A61K 9/48; A61K 9/4816; A61K 35/37; A61K 38/13; A61K 2035/115; A61K 9/0056; A61K 9/0058; A61K 41/0004; A61K 47/545; A61K 2035/11; A61K 31/454; A61K 31/733; A61K 35/17; A61K 38/00; A61K 47/554; A61K 9/0031; A61K 9/4891; A61K 31/438; A61K 31/45; A61K 31/4545; A61K 31/7004; A61K 31/7016; A61K 35/39; A61K 38/46; A61K 47/26; A61K 9/19; A61K 31/00; A61K 31/4035; A61K 31/435; A61K 31/439; A61K 31/451; A61K 31/4709; A61K 31/513; A61K 31/547; A61K 31/55; A61K 38/465; A61K 47/549; A61K 48/005; A61K 9/0029; A61K 9/2846; A23K 10/18; A23K 20/163; A23K 50/10; A23K 50/50; A23K 20/10; A23K 50/42; A23K 50/48; C12N 1/20; C12N 15/1072; C12N 15/113; C12N 15/115; C12N 2310/16; C12N 2320/10; C12N 9/22; C12N 15/907; C12N 15/1086; C12N 15/63; C12N 15/90; C12N 15/11; C12N 15/8216; C12N 15/85; C12N 15/902; C12N 2310/3513; C12N 2320/33; C12N 9/0008; C12N 9/0069; C12N 9/1096; C12N 9/78; C12N 9/88; C12N 9/96; A23V 2002/00; A23V 2200/3202; A23V 2200/3204; A23V 2200/322; A23V 2200/32; A23V 2250/28; A23V 2250/284; A23V 2250/5114; A23V 2250/54252; A23V 2250/156; A23V 2250/1842; A23V 2250/5424; A23V 2250/54246; A23V 2250/612; A23V 2250/70; A23V 2250/1592; A23V 2250/7056; A23V 2250/1868; A23V 2250/186; A23V 2250/1618; A23V 2250/1642; A23V 2250/1578; A23V 2250/161; A23V 2250/1588; A23V 2250/1846; A23V 2250/185; A23V 2250/1862; A23V 2250/1852; A23V 2250/706; A23V 2250/16; A23V 2250/1612; A23V 2250/1614; A23V 2250/1848; A23V 2250/1882; A23V 2250/304; A23V 2250/54242; A23V 2200/31; A23V 2200/304; A23V 2200/324; A23V 2250/5034; A23V 2250/54248; A23V 2250/5348; A23V 2250/1564; A23V 2250/1886; A23V 2200/224; A23V 2200/328; A23V 2200/332; A61P 25/24; A61P 25/28; A61P 25/22; A61P 3/02; A61P 1/00; A61P 1/04; A61P 1/12; A61P 29/00; A61P 1/16; A61P 35/00; A61P 19/02; A61P 25/00; A61P 1/14; A61P 11/00; A61P 17/00; A61P 25/18; A61P 37/00; A61P 3/00; A23C 2230/10; A23C 9/20; A23C 9/206; C12Q 1/6876; C12Q 2600/158; C12Q 2600/106; C12Q 2600/178; C12Q 1/6883; C12Q 2600/112; C12Q 1/18; C12Q 1/689; C12Q 1/6874; C12Q 1/6888; A23Y 2300/00; A23Y 2220/73; A23Y 2300/25; C12Y 304/21; C12Y 301/00; C12Y 304/21043; C12Y 102/01019; C12Y 113/12001; C12Y 206/01082; C12Y 305/03011; C12Y 401/01015; C12Y 401/01017; Y02A 50/473; Y02A 50/402; Y02A 50/475; Y02A 50/478; Y02A 50/481; Y02A 50/48; Y02A 50/469; Y02A 50/49; Y02A 90/26; Y02A 50/463; Y02A 50/401; Y02A 50/414; Y02A 50/479; Y02A 50/406; Y02A 50/411; Y02A 50/451; G01N 2800/044; G01N 2800/32; G01N 2333/605; G01N 2333/912; G01N 2800/04; G01N 2800/042; G01N 2800/52; G01N 33/66; G01N 33/6893; G16B 40/00; G16B 50/00; G16B 25/00; G16B 40/20; G16B 45/00; G16B 5/00; G16B 19/3418; G16H 40/67; G16H 50/20; H01L 2251/5338; H01L 27/3211; H01L 27/322; H01L 27/3272; H01L 51/0097; H01L 51/5234; H01L 51/5265; H01L 51/5281; H01L 51/5284; A23P 10/30; C07K 14/705; C07K 14/7051; C07K 14/70521; C07K 16/00; C07K 2317/622; C07K 2319/01; C07K 2319/03; C07K 2319/09; C07K 2319/33; C07K 2319/74; C07K 14/47; C07K 14/72; H05K 999/99; C07D 401/04; C07D 211/88; C07D 401/12; C07D 401/14; C07D 405/14; C07D 413/04; C07D 471/04; C07D 487/04; C07D 495/14; C07D 519/00; C07D 211/86; C07D 211/90; C07D 221/22; C07D 401/06; C07D 403/04; C07D 413/12; C07D 413/14; C07D 417/04; C07D 417/14; C07D 471/08; C07D 471/10; C07D 495/04; C07D 498/20; C12R 1/01
See application file for complete search history.

(56) References Cited

U.S. PATENT DOCUMENTS

| | | | | |
|---|---|---|---|---|
| 8,691,244 | B2* | 4/2014 | Mercenier | A23L 33/135 424/282.1 |
| 8,916,374 | B2* | 12/2014 | Mercenier | A61K 35/744 435/252.9 |
| 9,370,538 | B2* | 6/2016 | Petit | A61K 35/745 |
| 9,439,449 | B2* | 9/2016 | Holvoet | A23L 33/22 |
| 2004/0265279 | A1* | 12/2004 | Dinan | A61K 35/745 424/93.4 |
| 2012/0230956 | A1* | 9/2012 | McLean | A61K 35/74 424/93.4 |
| 2013/0273016 | A1* | 10/2013 | Faure | A23L 5/00 424/93.45 |
| 2013/0280225 | A1* | 10/2013 | Faure | A61K 31/702 424/93.45 |

(56) References Cited

U.S. PATENT DOCUMENTS

| | | | | |
|---|---|---|---|---|
| 2013/0344045 | A1* | 12/2013 | Faure | A23L 33/21 424/93.45 |
| 2016/0310557 | A1* | 10/2016 | Faure | A61K 9/0053 |

OTHER PUBLICATIONS

Pinto-Sanchez et al. "OP162 Bifidobacterium Longum NCC3001 Improves Depression and Reduces Brain Emotional Reactivity in Patients With Irritable Bowel Syndrome (IBS): A Randomized, Double Blend, Placebo-Controlled Trial" United European Gastroenterology Journal, 2015, vol. 3, No. 5, p. A53, XP002764838.

Bercik et al. "The anxiolytic effect of Bifidobacterium longum NCC3001 involves vagal pathways for gut-brain communication" Neurogastroenterol Motil., 2011, vol. 23, No. 12, pp. 1132-1139.

* cited by examiner

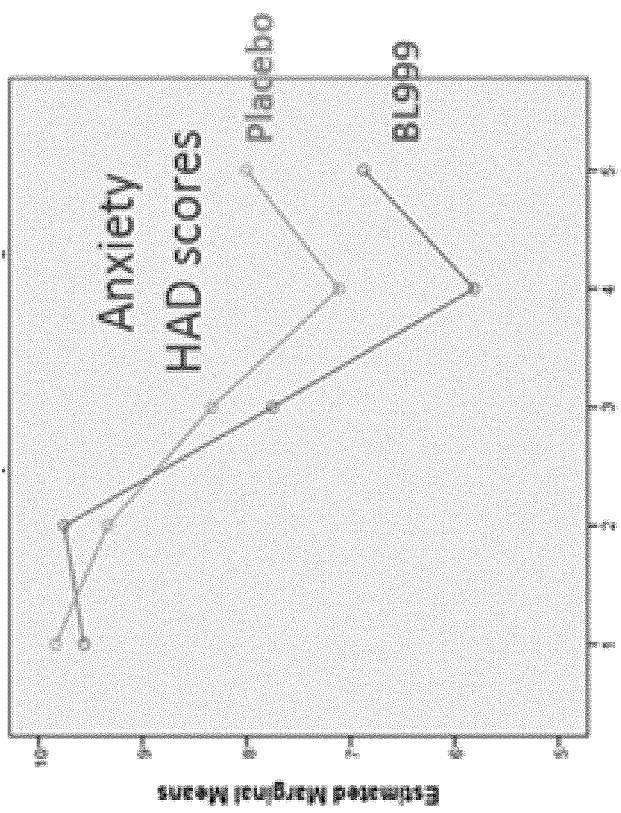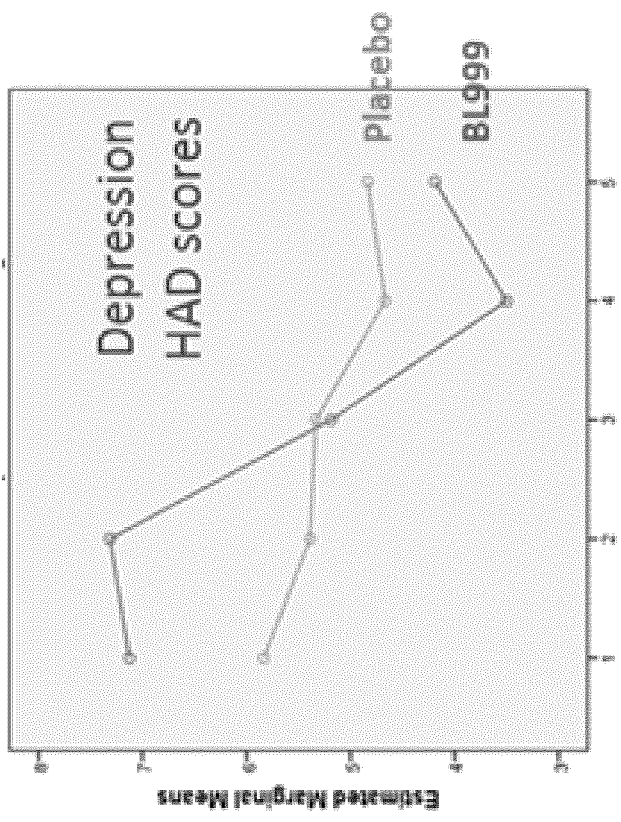
FIG. 3

FIG. 5

| | Physical Functioning (PF) Post-Treatment | Role Physical (RP) Post-Treatment | Bodily Pain (BP) Post-Treatment | General health (GH) Post-Treatment | Vitality (VT) Post-Treatment | Social functioning (SF) Post-Treatment | Role emotional (RE) Post-Treatment | Mental Health (MH) Post-Treatment |
|---|---|---|---|---|---|---|---|---|
| Mann-Whitney U | 106.000 | 90.000 | 152.500 | 136.500 | 109.000 | 134.000 | 120.000 | 135.500 |
| Wilcoxon W | 316.000 | 300.000 | 362.500 | 346.500 | 319.000 | 344.000 | 330.000 | 345.500 |
| Z | -1.991 | -2.582 | -.542 | -1.024 | -1.869 | -1.127 | -1.672 | -1.056 |
| Asymp. Sig. (2-tailed) | .047 | .010 | .588 | .306 | .062 | .260 | .094 | .291 |
| Exact Sig. [2*(1-tailed Sig.)] | .052[b] | .014[b] | .598[b] | .311[b] | .065[b] | .283[b] | .133[b] | .297[b] | a. Grouping Variable: Group
b. Not corrected for ties.

METHOD OF USING BIFIDOBACTERIUM LONGUM TO TREAT DEPRESSIVE SYMPTOMS

CROSS REFERENCE TO RELATED APPLICATIONS

The present application is a National Stage of International Application No. PCT/EP2016/070461, filed on Aug. 31, 2016, which claims priority to U.S. Provisional Patent Application No. 62/212,148, filed on Aug. 31, 2015, U.S. Provisional Patent Application No. 62/220,408, filed on Sep. 18, 2015, and U.S. Provisional Patent Application No. 62/236,639, filed on Oct. 2, 2015, the entire contents of which are being incorporated herein by reference.

BACKGROUND

The present disclosure generally relates to probiotic bacteria. Specifically, compositions and methods are disclosed that use *Bifidobacterium longum* NCC3001 (ATCC BAA-999) to treat or prevent a depressive symptom.

Depression has a significant negative impact on quality of life, including somatic and emotional symptoms. Depression is related to impaired neurotransmission, e.g. low neurotransmitter levels. As a result, compounds that increase neurotransmitter levels in the brain and thus enhance their transmission exhibit anti-depressant properties as well as beneficial effects for a variety of other mental disorders. The main neurotransmitters are serotonin, dopamine, norepinephrine, noradrenaline, acetylcholine, glutamate, gamma-amino-butyric acid, as well as neuropeptides. Increased neurotransmission is achieved by increasing the concentration of the neurotransmitter in the synaptic cleft, thus making the neurotransmitter available for increased or prolonged neurotransmission through inhibition of re-uptake into the pre-synaptic nerve end, or by preventing neurotransmitter catabolism by inhibition of degrading enzymes such as monoaminooxidase A and B (MAO A and MAO B, respectively).

Tricyclic antidepressant compounds (TCAs), for example imipramine, amitriptyline, and clomipramine, inhibit the re-uptake of serotonin and noradrenaline. These compounds are widely regarded as among the most effective antidepressants available, but they have a number of disadvantages because they interact with brain receptors such as cholinergic receptors. Most importantly, risks associated with overdoses of TCAs include acute cardiotoxicity.

Another class of antidepressant drugs is the selective serotonin re-uptake inhibitors (SSRIs) which include fluoxetine, paroxetine, sertraline, citalopram and fluvoxamine. SSRIs block the serotonin transporter (SERT), a high affinity sodium chloride-dependent neurotransmitter transporter that terminates serotonergic neurotransmission by uptake of serotonin, thus inhibiting re-uptake of serotonin alone. These compounds have been demonstrated to be effective in the treatment of depression and anxiety and are usually better tolerated than TCAs. These medications are typically started at low dosages and dosage level may be increased until they reach a therapeutic level. A common side effect is nausea. Other possible side effects include decreased appetite, dry mouth, sweating, infection, constipation, yawning, tremors, sleepiness and sexual dysfunction.

In addition, compounds that prevent the catabolism of neurotransmitters more broadly by inhibiting MAO A and MAO B exhibit antidepressant effects. The MAOs catalyse the oxidation of amino group containing neurotransmitters such as serotonin, noradrenaline, and dopamine.

Furthermore, modulators of neurotransmission exert pleiotropic effects on mental and cognitive functions.

These and other psychotropic drugs can lead to several side-effects such as dry mouth, blurry vision, lowered gastrointestinal motility or constipation, urinary retention, cognitive and/or memory impairment, drowsiness, confusion, restlessness, dizziness, hypersensitivity, changes in appetite and weight, sexual dysfunction, nausea and vomiting, hypotension, tachycardia, and occasionally irregular heart rhythms. Hallucinations, delirium and coma are some of the toxic effects caused by overdose. Therapies typically require an experienced trained professional and long-term therapy to achieve results.

Consequently, patients are subjected to expensive treatments which involve healthcare providers, and many patients are interested in alternative therapies which could minimize the side effects associated with high doses of drugs and yield additive clinical benefits.

Depressive symptoms that do not fulfill a diagnosis of depression are significant as well. For example, depressive symptoms and depression disorders not otherwise specified are more prevalent than major depression. According to the Diagnostic and Statistical Manual of Mental Disorders, 4th Edition (DSM-IV), periods of sadness are inherent aspects of the human experience. These periods should not be diagnosed as a Major Depressive Episode unless criteria are met for severity (i.e., five out of nine symptoms), duration (i.e., most of the day, nearly every day for at least 2 weeks), and clinically significant distress or impairment. The diagnosis "Depressive Disorder Not Otherwise Specified" may be appropriate for presentations of depressed mood with clinically significant impairment that do not meet criteria for duration or severity. "Depressive Disorder Not Otherwise Specified" includes disorders with depressive features that do not meet the criteria for Major Depressive Disorder. Examples of "Depressive Disorder Not Otherwise Specified" include pre-menstrual dysphoric disorder, minor depressive disorder, recurrent brief depressive disorder, and situations in which the clinician has concluded that a depressive disorder is present but is unable to determine whether the depressive disorder is primary, due to a general medical condition, or substance-induced.

SUMMARY

The present inventors surprisingly found that *Bifidobacterium longum* ATCC BAA-999 improves depressive symptoms and reduces brain emotional activity in patients to whom these bacteria are administered. As set forth in more detail later herein, the present inventors conducted a randomized, double blind, placebo-controlled trial. Psychopathology (high incidence of depression) plays a central role in irritable bowel syndrome (IBS), so this condition was used as a model for the clinical trial. The results demonstrated that six-week treatment with *B. longum* ATCC BAA-999 improved co-morbid depressive symptoms, overall gastrointestinal symptoms, and quality of life in patients with IBS.

Specifically, the study showed that administration of *B. longum* ATCC BAA-999 modulates behavior via gut-to-brain signaling. These effects appear to be mediated through down-regulation of the brain areas involved with the emotion control.

Six week treatment with *B. longum* ATCC BAA-999 in patients with non-constipation IBS improved depression scores, achieved adequate relief of IBS symptoms, improved quality of life physical scores, and down-regulated engagement of brain centers involved in the control of emotions and mood (amygdala and fronto—limbic regions) in response to fearful stimuli. The beneficial effect of the *B. longum* ATCC BAA-999 on depressive symptoms was maintained at one month post-treatment, while IBS symptoms and quality of life returned to baseline.

Without wishing to be bound by theory, the inventors presently believe that the underlying prophylactic and/or therapeutic mechanism of the *B. longum* ATCC BAA-999 is related to the modulation of the bidirectional microbial-gut-brain axis, possibly significantly associated with psychological factors. In this regard, IBS is believed to result from the interaction of altered gut physiology and psychological factors via the gut-brain axis, where brain and gut symptoms are reciprocally influencing each other. Intestinal microbiota play a central role in this "dialogue" between the gut and the brain, and the present inventors believe that *B. longum* ATCC BAA-999 acts on the microbiota-gut-brain axis to reduce depressive symptoms in IBS.

Accordingly, in a general embodiment, the present disclosure provides a method of treating a depressive symptom. A "depressive symptom" is defined later herein and includes but is not limited to major depression disorder. Throughout this disclosure and in the claims, the term "depressive symptom" also encompasses symptoms associated with clinical and subclinical depression and the DSM-IV classification "depressive disorder not otherwise specified" (e.g. a patient with depressive features that do not fulfill criteria for major depression). A "depressive symptom" also encompasses depressive symptoms from depressive states not fulfilling DSM-IV disorder criteria. The method comprises administering an edible composition comprising a therapeutically effective amount of *B. longum* ATCC BAA-999 to an individual having a depressive symptom.

In an embodiment, the depressive symptom is a primary psychiatric disorder not caused by an underlying medical condition or drug.

In an embodiment, the depressive symptom is a secondary condition caused by an underlying medical condition selected from the group consisting of a neurological disorder, a metabolic disorder, an endocrine disease, a cardiovascular disease, a pulmonary disease, a cancer, an autoimmune disease, and combinations thereof. For example, the depressive symptom can be one or more depressive symptoms arising from the underlying medical condition.

In an embodiment, the depressive symptom is selected from the group consisting of depressed mood; sadness; anxiety; "empty" feelings; loss of interest or pleasure; irritability; restlessness; changes in appetite or weight; sleep disturbances; lack of or decreased energy; feelings of worthlessness; guilt; helplessness; anger and hostility; difficulty in thinking, concentrating, or making decisions; hopelessness; tiredness; fatigue; memory difficulties; tearfulness; brooding; phobias; excessive worry over physical health; sexual dysfunction; persistent physical symptoms that do not respond to treatment; and combinations thereof.

In an embodiment, the composition further comprises an ingredient selected from the group consisting of a fat, a protein, a carbohydrate and combinations thereof.

In an embodiment, the composition comprises a prebiotic. The prebiotic can be selected from the group consisting of an oligosaccharide, a dietary fiber, and a combination thereof.

In an embodiment, the composition is administered to the individual each day of a time period that is at least six weeks.

In an embodiment, at least a portion of the *B. longum* ATCC BAA-999 is alive. The composition can comprise $10^4$ to $10^{11}$ cfu of the *B.* ATCC BAA-999 per g of dry weight of the composition. The composition can be administered to the individual in a daily dose comprising between $10^4$ and $10^{12}$ cfu of the *B.* ATCC BAA-999. The daily dose of the composition can be administered to the individual each day of a time period that is at least six weeks.

In an embodiment, at least a portion of the *B. longum* ATCC BAA-999 is non-replicating cells. The composition can be administered to the individual in a daily dose comprising between $10^4$ and $10^{10}$ of the non-replicating cells of *B. longum* ATCC BAA-999. The composition can comprise between $10^2$ and $10^8$ of the non-replicating cells of *B. longum* ATCC BAA-999 per g of dry weight of the composition. The daily dose of the composition can be administered to the individual each day of a time period that is at least six weeks.

In an embodiment, the method is a natural therapy.

In an embodiment, the individual has a depressive state or depressive disorder selected from the group consisting of subclinical depression, the DSM-IV classification "a depressive disorder not otherwise specified," depressive symptoms not fulfilling DSM-IV disorder criteria, and combinations thereof.

In another embodiment, the present disclosure provides a method of preventing a depressive symptom. The method comprises administering to an individual at risk thereof an edible composition comprising a prophylactically effective amount of *B. longum* ATCC BAA-999.

In an embodiment, the method comprises identifying the individual as being at risk of a depressive symptom.

In an embodiment, the depressive symptom that is prevented is selected from the group consisting of depressed mood; sadness; anxiety; "empty" feelings; loss of interest or pleasure; irritability; restlessness; changes in appetite or weight; sleep disturbances; lack of or decreased energy; feelings of worthlessness; guilt; helplessness; anger and hostility; difficulty in thinking, concentrating, or making decisions; hopelessness; tiredness; fatigue; memory difficulties; tearfulness; brooding; phobias; excessive worry over physical health; sexual dysfunction; persistent physical symptoms that do not respond to treatment; and combinations thereof.

In an embodiment, the composition is administered to the individual each day of a time period that is at least six weeks.

In another embodiment, the present disclosure provides a method of making an edible composition for treating or preventing a depressive symptom. The method comprises incorporating a therapeutically effective amount or a prophylactically effective amount of *B. longum* ATCC BAA-999 into a food product comprising at least one ingredient selected from the group consisting of a fat, a protein and a carbohydrate.

In another embodiment, the present disclosure provides a method of supplementing a regimen for treatment or prevention of a depressive symptom. The regimen that is supplemented comprises administering to an individual in need or at risk thereof a pharmaceutical composition. The method comprises administering an edible composition comprising a therapeutically effective amount or a prophylactically effective amount of *B. longum* ATCC BAA-999 to the individual, in addition to the pharmaceutical composition.

An advantage of one or more embodiments provided by the present disclosure is a composition comprising a bacterial strain that is effective, readily available, low-priced, and safe to administer without unwanted side effects which can be used to treat or prevent a depressive symptom.

Another advantage of one or more embodiments provided by the present disclosure is to treat or prevent a depressive symptom using a bacterial strain that is commercially available and already tested and found to be acceptable for addition to food products.

Another advantage of one or more embodiments provided by the present disclosure is to provide a better safety profile relative to known anti-depressants.

A further advantage of one or more embodiments provided by the present disclosure is to minimize or avoid completely the side effects from known anti-depressants.

An additional advantage of one or more embodiments provided by the present disclosure is to improve the effect of and/or reduce the dose of one or more known anti-depressants which are co-administered with the composition disclosed herein.

Yet another advantage of one or more embodiments provided by the present disclosure is to minimize or avoid completely unnecessary costs related to healthcare assistance.

Another advantage of one or more embodiments provided by the present disclosure is to achieve prolonged anti-depressive effects even after the treatment is discontinued.

A further advantage of one or more embodiments provided by the present disclosure is to use to treat or prevent a depressive symptom using a bacterial strain that provides other health benefits as well.

Additional features and advantages are described herein and will be apparent from the following Detailed Description and the Figures.

BRIEF DESCRIPTION OF THE FIGURES

FIG. 3 shows graphs demonstrating the secondary outcome from administration of *B. longum* ATCC BAA-999, improvement in depression and anxiety continuous scores.

FIGS. 4 and 5 respectively show graphs and a table demonstrating that administration of *B. longum* ATCC BAA-999 significantly improved the physical global domain as well as general physical health (physical functioning) and problems with work of other daily activities (role physical) and resulted in an improvement trend in the mental subdomains of vitality and role emotional.

DETAILED DESCRIPTION

Figure 1:
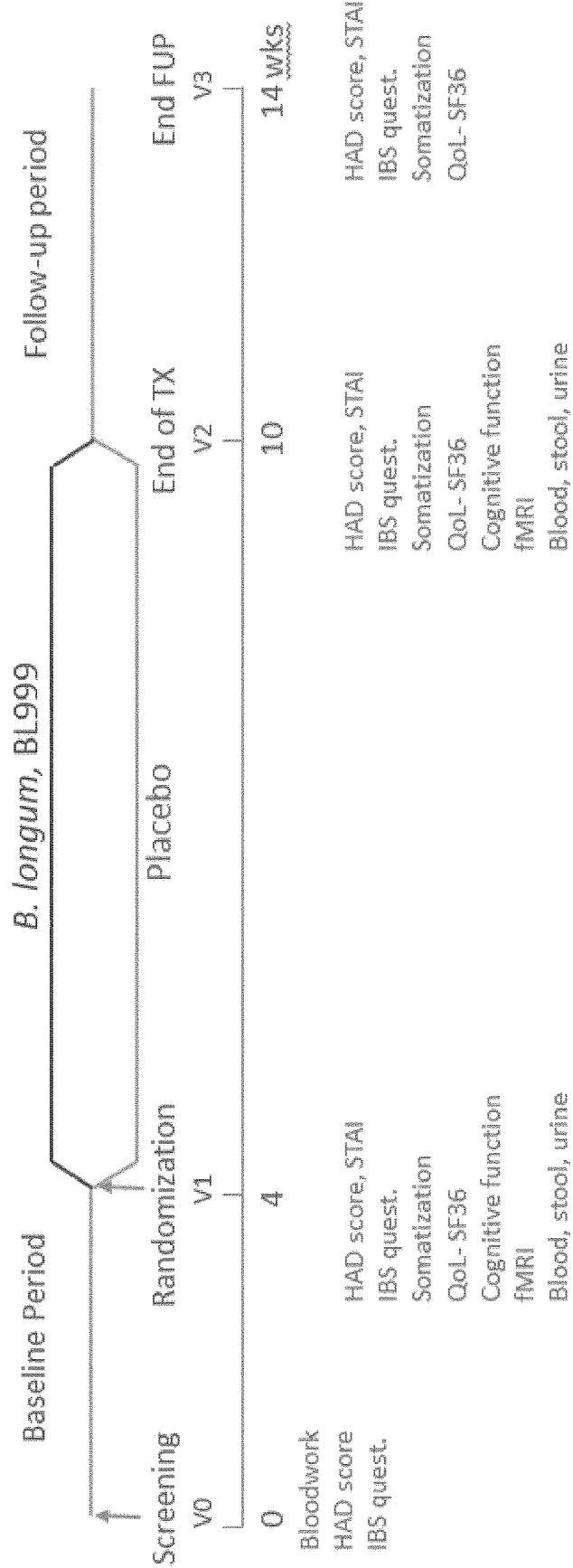
FIG. 1 shows the design of the clinical trial disclosed herein.

As used in this disclosure and the appended claims, the singular forms "a," "an" and "the" include plural referents unless the context clearly dictates otherwise. Thus, for example, reference to "a bacterial strain" or "the bacterial strain" includes two or more bacterial strains.

The words "comprise," "comprises" and "comprising" are to be interpreted inclusively rather than exclusively. Likewise, the terms "include," "including" and "or" should all be construed to be inclusive, unless such a construction is clearly prohibited from the context.

Nevertheless, the compositions disclosed herein may lack any element that is not specifically disclosed. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

As used herein, "about" and "approximately" are understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number.

Furthermore, all numerical ranges herein should be understood to include all integers, whole or fractions, within the range. The term "between" includes the end points of the identified range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the terms "individual" and "patient" are understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

The terms "treatment" and "treating" include any effect that results in the improvement of the condition or disorder, for example lessening, reducing, modulating, or eliminating the condition or disorder. The term does not necessarily imply that a subject is treated until total recovery. Non-limiting examples of "treating" or "treatment of" a condition or disorder include: (1) inhibiting the condition or disorder, i.e. arresting the development of the condition or disorder or its clinical symptoms and (2) relieving the condition or disorder, i.e. causing the temporary or permanent regression of the condition or disorder or its clinical symptoms. A treatment can be patient- or doctor-related.

The terms "prevention" or "preventing" mean causing the clinical symptoms of the referenced condition or disorder to not develop in an individual that may be exposed or predisposed to the condition or disorder but does not yet experience or display symptoms of the condition or disorder. The terms "condition" and "disorder" mean any disease, condition, symptom, or indication.

The relative terms "improved," "increased," "enhanced" and the like refer to the effects of the composition comprising B. longum ATCC BAA-999 (disclosed herein) relative to a composition lacking B. longum ATCC BAA-999 but otherwise identical.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the essential elements and limitations described herein, as well as any additional or optional ingredients, components, or limitations described herein or otherwise useful in a diet.

As used herein, "complete nutrition" contains sufficient types and levels of macronutrients (protein, fats and carbohydrates) and micronutrients to be sufficient to be a sole source of nutrition for the animal to which the composition is administered. Individuals can receive 100% of their nutritional requirements from such complete nutritional compositions.

An aspect of the present disclosure is a composition comprising B. longum ATCC BAA-999 in an amount effective to treat or prevent a depressive symptom in an individual, preferably a human. B. longum ATCC BAA-999 is also known as BL999 and NCC3001 and may be obtained commercially from specialist suppliers, for example from Morinaga Milk Industry Co. Ltd. of Japan under the trademark BB536. The term "B. longum ATCC BAA-999" includes the bacterium, parts of the bacterium, and/or a growth medium fermented by the bacterium. In an embodiment, the composition can be administered to the individual daily for a time period that is at least six weeks and preferably provides anti-depressive effects even after administration ends.

In some embodiments, the method is a natural therapy. For example, the composition can consist of natural ingredients, and preferably the individual is not administered any artificial composition such as a synthetic pharmaceutical compound. In other embodiments, the composition supplements a regimen in which a pharmaceutical composition is also administered.

In some embodiments, the composition treats or prevents a depressive symptom as a primary psychiatric disorder, i.e., the depressive symptom is not caused by an underlying medical condition or drug. For example, the individual to whom the composition is administered can have a depressive symptom that does not have an underlying condition such as a gastrointestinal disorder.

In other embodiments, the depressive symptom treated or prevented by the composition is the result of an underlying condition. Non-limiting examples of underlying conditions that can cause a depressive symptom that is a secondary condition include a neurological disorder (e.g., dementia), a metabolic disorder (e.g., an electrolyte disturbance), an endocrine disease (e.g. a thyroid abnormality), a cardiovascular disease (e.g., a heart attack), a pulmonary disease (e.g., chronic obstructive pulmonary disease), a cancer, and an autoimmune disease (e.g., rheumatoid arthritis).

As used herein, a "depressive symptom" includes any feeling of sadness and loss of interest, and a depressive symptom is typically based on an imbalance of one or more neurotransmitters. Non-limiting examples of specific forms of a depressive symptom include typical or atypical symptoms, such as depressed mood; sadness; anxiety; "empty" feelings; loss of interest or pleasure; irritability; restlessness; changes in appetite or weight; sleep disturbances; lack of or decreased energy; feelings of worthlessness; guilt; helplessness; anger and hostility; difficulty in thinking, concentrating, or making decisions; hopelessness; tiredness; fatigue; memory difficulties; tearfulness; brooding; phobias; excessive worry over physical health; sexual dysfunction; persistent physical symptoms that do not respond to treatment (e.g. headache and chronic pain); and any combination thereof. An individual "at risk" of a depressive symptom includes an individual who has been in remission from a depressive symptom and is now diagnosed with a relapse or a predisposition to a relapse.

These depressive symptoms are frequently part of and/or found in depressive states or depressive disorders, such as clinical and subclinical depressive states, the DSM-IV classification "a depressive disorder not otherwise specified," depressive symptoms not fulfilling DSM-IV disorder criteria, major and minor depressive disorders, pre-menstrual dysphoric disorder, post-menopausal depressive symptoms, depressive disorders associated with aging, major depressive disorder (including single episode and recurrent), unipolar depression, bipolar depression, acute depression, chronic depression, dysthymia, climacteric depressive symptoms, treatment-refractory depression, treatment-resistant depression, seasonal affective disorders, and any combination thereof.

Nevertheless, these depressive symptoms can be found sub-clinically or not associated with these depressive states/disorders (e.g., not part of a syndrome or psychiatric disorder). Accordingly, the present disclosure is not limited to depressive symptoms associated with the above-noted depressive states/disorders.

A depressive symptom can be diagnosed using standard clinical criteria, e.g., the DSM-IV-TR system. For example, the DSM-IV system for diagnosing major depressive disorder requires the presence of at least five out of the ten depressive symptoms including depressed mood or irritable, decreased interest or pleasure, significant weight change (5%) or change in appetite, change in sleep (e.g., insomnia or hypersomnia), change in activity, fatigue or loss of energy, guilt or worthlessness, diminished concentration, and suicidality. In addition, the symptoms should be present for at least two weeks, and each symptom should be at sufficient severity for nearly every day.

Generally, a depressive symptom is evaluated by a clinician using, e.g., the criteria list in the DSM-IV or efficacy measures (neuropsychological assessments) such as the Mini-Mental State Examination (MMSE), the Hamilton Depression Rating Scale (HAMD-28 or HAMD-7), the Clinical Global Impression (CGI) Scale, the Montgomery-Asberg Depression Rating Scale (MADRS), the Beck Depression Inventory (BDI), the Zung Self-Rating Depression Scale, the Wechsler Depression Rating Scale, the Raskin Depression Rating Scale, the Inventory of Depressive Symptomatology (IDS), and the Quick Inventory of Depressive Symptomatology (QIDS). For example, a measurable improvement of a depressive symptom includes any clinically significant decline in a measurable marker, such as measuring markers for a depressive symptom in the blood, e.g., red blood cell folate, serum folate, serum MTHF, or assessing the degree of a depressive symptom, e.g., using a neuropsychological assessment.

For example, a score of 0-7 on HAMD is typically considered to be normal. Scores of 20 or higher indicate moderate, severe, or very severe depressive symptoms. Questions 18-21 may be recorded to give further information about the depressive symptom (such as whether diurnal variation or paranoid symptoms are present), but are not necessary part of the scale. Thus, a reduction of symptoms can be considered clinically relevant if, e.g., the HAMD score is decreased to under, e.g., 20.

Accordingly, some embodiments of the methods of treating or preventing a depressive symptom disclosed herein comprise diagnosing the individual as having the depressive symptom or at risk of developing the depressive symptom, e.g., before initiating administration of the composition comprising B. longum ATCC BAA-999. In some embodiments, the composition is administered to an individual being screened for a depressive symptom (e.g., during a routine physical), for example, in accordance with the criteria listed in DSM-IV or ICD-10.

The DSM-IV and ICD-10 provide a common language and standard criteria for the classification of mental disorders, and have been commonly used by a suitably trained general practitioner, or by a psychiatrist or psychologist for diagnosis of a depressive symptom. Symptoms of a depressive state can include, but are not limited to, problems concentrating, remembering, and/or making decisions; changes in eating and/or sleeping habits; a loss of interest in enjoyable activities; difficulty going to work or taking care of daily responsibilities; feelings of guilt and/or hopelessness; slowed thoughts and/or speech; preoccupation with thoughts of death or suicide; anhedonia; low energy levels; psychomotor retardation; agitation; reduced cognition; or combinations thereof. One of skill in the art can determine the score or rating of a depressive symptom based on DSM-IV or ICD-10.

Additionally or alternatively, other scales or criteria for classification of mental disorders known in the art can be used to determine the degree of a depressive symptom, e.g., Maier or HAMD-7 scale, social functioning questionnaire (SFQ), visual analogue scale (VAS), and/or cognitive and physical function questionnaire (CPFQ).

During diagnosis for a depressive symptom, a practitioner can also assess the patient's medical history, discuss the individual's current way of regulating their mood (healthy or otherwise) such as alcohol and drug use, and/or perform a mental state examination, which is an assessment of the person's current mood and thought content, in particular the presence of themes of hopelessness or pessimism, self-harm or suicide, and an absence of positive thoughts or plans. Additionally, a practitioner can generally perform a medical examination to rule out other non-cognitive causes of depressive symptoms. For example, blood tests measuring TSH and thyroxine can be used to exclude hypothyroidism; basic electrolytes and serum calcium can rule out a metabolic disturbance; and a full blood count including ESR can rule out a systemic infection or chronic disease. Testosterone levels can also be evaluated to diagnose hypogonadism, a cause of depressive symptoms in men.

Any genetic or biomarker methods known in the art can also be used for diagnosis of a depressive symptom. For example, U.S. Pat. App. Pub. No. US 2010/0273153 (herein incorporated by reference in its entirety) describes that the presence of TG7AT haplotype can be indicative of predisposition to major depressive disorder. Additional genetic markers for a depressive symptom such as ATP2A2, SCYAS, STIP1, EEF1A1, GRB10, CASP6, TSSC1, RAB9, NFATC3, TPR, and any others listed in, for example, U.S. Pat. App. Pub. No. US 2005/0239110 (herein incorporated by reference in its entirety) can also be used for diagnosing a depressive symptom.

In some embodiments, the individual has been diagnosed with or suspected of having or developing major depressive disorder. A major depressive episode is characterized by the presence of a severely depressed mood that persists for at least two weeks. Episodes can be isolated or recurrent and can be categorized by a skilled practitioner as mild (few symptoms in excess of minimum criteria), moderate, or severe (marked impact on social or occupational functioning).

B. longum ATCC BAA-999 was deposited by the Assignee of the present application as NCC 3001 on Jan. 29, 2001 at the Institut Pasteur, 28 rue du Docteur Roux, F-75024 Paris Cedex 15, France. All restrictions upon public access to the deposits will be irrevocably removed upon grant of a patent on this application, and the deposits will be replaced if viable samples cannot be dispensed by the depository.

The B. longum ATCC BAA-999 may be cultured according to any suitable method. B. longum ATCC BAA-999 may be added to a food product in a freeze-dried or spray-dried form, for example, to form the composition.

The composition may be orally and/or enterally administrable; for example in the form of a powder for reconstitution with milk or water. The composition may be selected from the group consisting of a food composition, a pet food composition, a dietary supplement, a nutraceutical, a nutritional formula, a drink, and a medical composition. In a preferred embodiment, the composition is a food product intended for an adult such as a human adult.

A food composition has the advantage that such a composition can be distributed in not only pharmacies and drug stores but also in supermarkets. The generally pleasant taste of food compositions will further contribute to the acceptance of the product. Non-limiting examples of suitable food compositions include yogurts, milk, flavored milk, ice cream, ready-to-eat desserts, malt drinks, ready-to-eat dishes, instant dishes, drinks for humans, and food compositions representing a complete or a partial diet.

The composition may further contain one or more of the following: a protective hydrocolloid (such as a gum, a protein, a modified starch), a binder, a film-forming agent, an encapsulating agent, a wall/shell material, a matrix compound, a coating, an emulsifier, a surface active agent, a solubilizing agent (such as an oil, a fat, a wax, a lecithin), an adsorbent, a carrier, a filler, a co-compound, a dispersing agent, a wetting agent, a processing aid (such as a solvent), a flowing agent, a taste masking agent, a weighting agent, a jellifying agent, a gel forming agent, an antioxidant or an antimicrobial. The composition may also contain a conventional pharmaceutical additive, adjuvant, excipient or diluent, including, but not limited to, water, gelatin of any origin, vegetable gum, ligninsulfonate, talc, a sugar, a starch, gum arabic, a vegetable oil, polyalkylene glycol, a flavoring agent, a preservative, a stabilizer, a, emulsifying agent, a buffer, a lubricant, or a colorant. Such further components are preferably selected having regard to their suitability for the intended recipient. In an embodiment, the composition is a nutritionally complete formula.

The composition can comprise a protein. Non-limiting examples of suitable proteins include animal proteins (such as milk protein, meat protein or egg protein), a vegetable protein (such as soy protein, wheat protein, rice protein, or pea protein); mixtures of free amino acids; or combinations thereof. Milk proteins such as casein and whey, and soy proteins are particularly preferred.

The proteins may be intact, hydrolyzed, or a mixture of intact and hydrolyzed proteins. Partially hydrolyzed proteins (degree of hydrolysis between 2 and 20%) may be advantageous for human subjects and/or animals at risk of developing cows' milk allergy. Furthermore, pre-hydrolyzed protein sources are generally easier digested and absorbed by an impaired gastro-intestinal tract.

If hydrolyzed proteins are used, the hydrolysis process may be carried out as desired and as known in the art. For example, a whey protein hydrolysate may be prepared by enzymatically hydrolyzing the whey fraction in one or more steps. If the whey fraction used as the starting material is substantially lactose-free, the protein can suffer much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a carbohydrate and/or a source of fat. If the composition includes a fat, the fat preferably provides 5% to 40% of the energy of the composition; for example 20% to 30% of the energy. A suitable fat profile may be obtained using a blend of canola oil, corn oil and high-oleic acid sunflower oil.

The carbohydrate preferably provides 40% to 80% of the energy of the composition. Non-limiting examples of suitable carbohydrates include sucrose, lactose, glucose, fructose, corn syrup solids, maltodextrins, and mixtures thereof. Additionally or alternatively, a dietary fiber may be added. Dietary fiber passes through the small intestine undigested by enzymes and functions as a natural bulking agent and laxative. Dietary fiber may be soluble or insoluble and generally a blend of the two types is preferred. Non-limiting examples of suitable dietary fibers include soy, pea, oat, pectin, guar gum, partially hydrolyzed guar gum, gum Arabic, fructo-oligosaccharides, acidic oligosaccharides, galacto-oligosaccharides, sialyl-lactose and oligosaccharides derived from animal milks. A preferred fiber blend is a mixture of inulin with shorter chain fructo-oligosaccharides. In an embodiment, the fiber content is between 2 and 40 g/L of the composition, for example between 4 and 10 g/L.

The composition may comprise minerals and/or micronutrients such as trace elements and vitamins in accordance with the recommendations of Government bodies such as the USRDA. For example, the composition may comprise, per daily dose, one or more of the following micronutrients, preferably in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, and/or 3 to 10 iug Vitamin E.

One or more food grade emulsifiers may be incorporated into the composition, such as diacetyl tartaric acid esters of mono- and di-glycerides, lecithin, and/or mono- and di-glycerides. Suitable salts and stabilizers may be included.

In an embodiment, the composition comprises an additional food grade micro-organism (i.e., in addition to the *B. longum* ATCC BAA-999). "Food grade" micro-organisms are micro-organisms that are safe for use in food. The food grade micro-organisms can comprise food-grade yeast. The food grade bacteria may be selected from the group consisting of lactic acid bacteria, bifidobacteria, propionibacteria and mixtures thereof. Non-limiting examples of suitable food grade yeast include *Saccharomyces cerevisiae* and/or *Saccharomyces boulardii*.

The food grade bacteria can comprise additional probiotic bacteria, although in some embodiments the *B. longum* ATCC BAA-999 is the only probiotic bacteria in the composition. "Probiotic" means microbial cell preparations or components of microbial cells with a beneficial effect on the health or well-being of the host. (Salminen S., Ouwehand A., Benno Y. et al "Probiotics: how should they be defined" Trends Food Sci. Technol. 1999:10 107-10).

Probiotic bacteria are preferably selected from the group consisting of lactic acid bacteria, bifidobacteria, propionibacteria and mixtures thereof. Probiotic bacteria may be any lactic acid bacteria or bifidobacteria with established probiotic characteristics. For example, probiotic bacteria may be capable of promoting the development of a bifidogenic intestinal microbiota.

Non-limiting examples of suitable probiotic bacteria include *Bifidobacterium, Lactobacillus, Streptococcus, Saccharomyces* and mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* and mixtures thereof, preferably selected from the group consisting of *Lactobacillus johnsonii* (NCC533; CNCM 1-1225), *Bifidobacterium longum* (NCC490; CNCM 1-2170), *Bifidobacterium longum* (NCC2705; CNCM 1-2618), *Bifidobacterium lactis* (2818; CNCM 1-3446), *Lactobacillus paracasei* (NCC2461; CNCM 1-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

In a preferred embodiment, the composition comprises at least one prebiotic. "Prebiotic" means a food substance intended to promote the growth of probiotic bacteria in the intestines. A prebiotic can promote the growth of certain food grade bacteria, in particular growth of probiotic bacteria, in the intestines and can thus enhance the effect of *B. longum* ATCC BAA-999 and any additional probiotic bacteria. Preferably the prebiotic is selected from the group consisting of oligosaccharides and optionally fructose, galactose, mannose, soy and/or inulin; dietary fibers; or mixtures thereof.

At least a portion of the *B. longum* ATCC BAA-999 may be living bacterium. Additionally or alternatively, at least a portion of the *B. longum* ATCC BAA-999 may be inactivated non-replicating bacterium.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no turbidity in liquid growth medium after inoculation with different concentrations of bacterial preparations ("non-replicating" samples) and incubation under appropriate conditions (aerobic and/or anaerobic atmosphere for at least 24 h). In some embodiments, such as special sterile food products or medicaments, a non-replicating form of the *B. longum* ATCC BAA-999 may be preferable. For example, at least 80%, preferably at least 90%, more preferably at least 95% of the *B. longum* ATCC BAA-999 can be non-replicating in the composition.

In an embodiment, at least a part of the *B. longum* ATCC BAA-999 are alive in the composition and preferably arrive alive in the intestine. For example, at least 5%, preferably at least 10%, more preferably at least 15% of the *B. longum* ATCC BAA-999 can be viable in the composition. As a result, the alive *B. longum* ATCC BAA-999 can persist in the intestine and may increase their effectiveness by multiplication. The alive *B. longum* ATCC BAA-999 may also be effective by interacting with the commensal bacteria and/or the host.

In therapeutic applications, the composition is administered in an amount sufficient to at least partially cure or arrest the symptoms of the condition and its complications. An amount adequate to accomplish this purpose is defined as "a therapeutically effective dose". Amounts effective for this purpose will depend on a number of factors known to those of skill in the art, such as the severity of the condition and the weight and general state of the patient.

In prophylactic applications, the composition can be administered to a patient susceptible to or otherwise at risk of a particular condition in an amount that is sufficient to at least partially reduce the risk of developing the condition. Such an amount is "a prophylactically effective dose." Again, the precise amounts depend on a number of patient-specific factors, such as the patient's state of health and weight.

The composition is preferably administered in an amount that provides a therapeutically effective dose and/or in a prophylactic effective dose of the *B. longum* ATCC BAA-999. If at least a portion of the *B. longum* ATCC BAA-999 is present in a viable form, the *B. longum* ATCC BAA-999 is theoretically effective in any concentration because the *B. longum* ATCC BAA-999 can colonize the gut and multiply therein.

Nevertheless, a daily dose of the composition preferably provides between $10^4$ and $10^{12}$ cfu (colony forming units) of the *B. longum* ATCC BAA-999, more preferably from $10^4$ to $10^{11}$ cfu, most preferably from $10^4$ to $10^{10}$ cfu. The composition may comprise between $10^2$ and $10^{10}$ cfu, preferably $10^2$ to $10^9$ cfu, more preferably $10^2$ to $10^8$ cfu of the *B. longum* ATCC BAA-999 per gram dry weight of the composition.

In the case of inactivated and/or non-replicating *B. longum* ATCC BAA-999, the composition can comprise between $10^2$ and $10^{10}$ non-replicating cells of the *B. longum* ATCC BAA-999 per gram of dry weight of the composition, preferably $10^3$ to $10^8$ non-replicating cells per gram of dry weight of the composition, more preferably $10^5$ to $10^8$ non-replicating cells per gram of dry weight of the composition.

Non-replicating micro-organisms do not form colonies, so the term "cells" indicates the amount of non-replicating micro-organisms obtained from the specified amount of replicating bacterial cells. This amount includes micro-organisms that are inactivated, non-viable or dead, or present as fragments such as DNA or cell wall materials.

The composition may be a powder having a water activity less than 0.2, preferably less than 0.15. The composition may be a shelf-stable powder. The low water activity can provide this shelf stability and can ensure that the *B. longum* ATCC BAA-999 and any additional probiotic micro-organism will remain viable even after long storage times. Water activity ($a_w$) is a measurement of the energy status of the water in a system and is defined as the vapor pressure of water divided by that of pure water at the same temperature; therefore, pure distilled water has a water activity of exactly one.

Additionally or alternatively, the *B. longum* ATCC BAA-999 and any additional probiotic micro-organism may be provided in an encapsulated form. Encapsulation of the bacteria can have therapeutical and technical advantages. For example, encapsulation can increase the survival of the bacteria and thus the number of live bacteria which arrive in the intestine. Furthermore, the bacteria can be gradually released, allowing a prolonged action of the bacteria on the health of the subject. For example, the bacteria may be freeze or spray dried and incorporated into a gel.

Another aspect of the present disclosure is a method of making an edible composition for treating or preventing a depressive symptom. The method can comprise incorporating a therapeutically effective or a prophylactically effective amount of *B. longum* ATCC BAA-999 into a food product comprising at least one of a protein, a fat or a carbohydrate. The food product can be nutritionally complete.

Example

The following non-limiting example is a randomized, double blind, placebo-controlled trial illustrative of *B. longum* ATCC BAA-999 improving a depressive symptom.

Introduction:

Specific probiotic bacteria can improve gut symptoms of IBS, however, their efficacy in treating co-morbid anxiety or a depressive symptom in this population is unknown. *B. longum* ATCC BAA-999 was previously shown to normalize anxiety-like behavior and hippocampal neurotrophin levels in murine models of low-grade gut inflammation. The present inventors also have unpublished data in depression models in mice and also showing improved sleeping patterns in mice.

Aims & Methods:

To evaluate the effects of *B. longum* ATCC BAA-999 on anxiety and depressive symptoms in patients with IBS and to study the underlying mechanisms, the present inventors conducted a randomized, double-blind, placebo-controlled, single center study in adult patients with IBS with diarrhea or mixed stool pattern (Rome III criteria) and mild to moderate anxiety and/or a depressive symptom. There were no differences in demographics and baseline data between the two groups, except for HAD-D scores, which were higher in *B. longum* group (p=0.046).

*B. longum* ATCC BAA-999 (1.0E+10 CFU daily) or placebo (maltodextrin) was administered daily for six weeks. Validated questionnaires were used to assess anxiety and a depressive symptom (HAD score (Hospital Anxiety and Depression) and STAI (State-Trait Anxiety Inventory) score), IBS symptoms (adequate relief question, IBS Birmingham and Bristol scale), quality of life (SF-36) and somatization (PHQ-15) before administration, at the end of administration, and one month after the treatment (followup). This experimental design is shown in FIG. 1.

The present inventors assessed brain activation patterns using the backward masked fear paradigm (fMRI), cognitive function (memory and concentration), serum BDNF and inflammatory markers, and gut microbiota profiles (16S rRNA Illumina). The fMRI paradigm utilized Blood Oxygenation Level Dependent (BOLD) activation in response to the presentation of emotional stimuli (fear and happy faces) that were masked by a neutral face, measured over four consecutive fMRI scan acquisitions in the scanner. The amygdala was selected as a priori region of interest. This analysis was performed on all subjects.

Results:

The present inventors randomized 44 patients, and 38 of them (*B. longum* ATCC BAA-999=18, placebo=20) completed the study. The results are shown in FIGS. 2-6. At six weeks, depression scores improved in patients treated with *B. longum* ATCC BAA-999 compared with placebo (RR 2.94, 95% CI 1.05-8.23, p=0.01), and this beneficial effect was maintained at follow-up. More patients treated with *B. longum* ATCC BAA-999 than placebo reported adequate relief of overall IBS symptoms (RR 2.1, 95% CI 1.15-3.83, p=0.02) but no statistically significant changes were found in the IBS Birmingham scores. The physical subdomain of quality of life improved in the group treated with *B. longum* ATCC BAA-999 compared with placebo (p=0.03, Mann-Whitney U=228.5), with trends for improvement in the mental subdomains of vitality and emotional role functioning.

The beneficial effect of *B. longum* ATCC BAA-999 on a depressive symptom was maintained at one month post-treatment, while IBS symptoms and quality of life returned to baseline.

Figure 2:
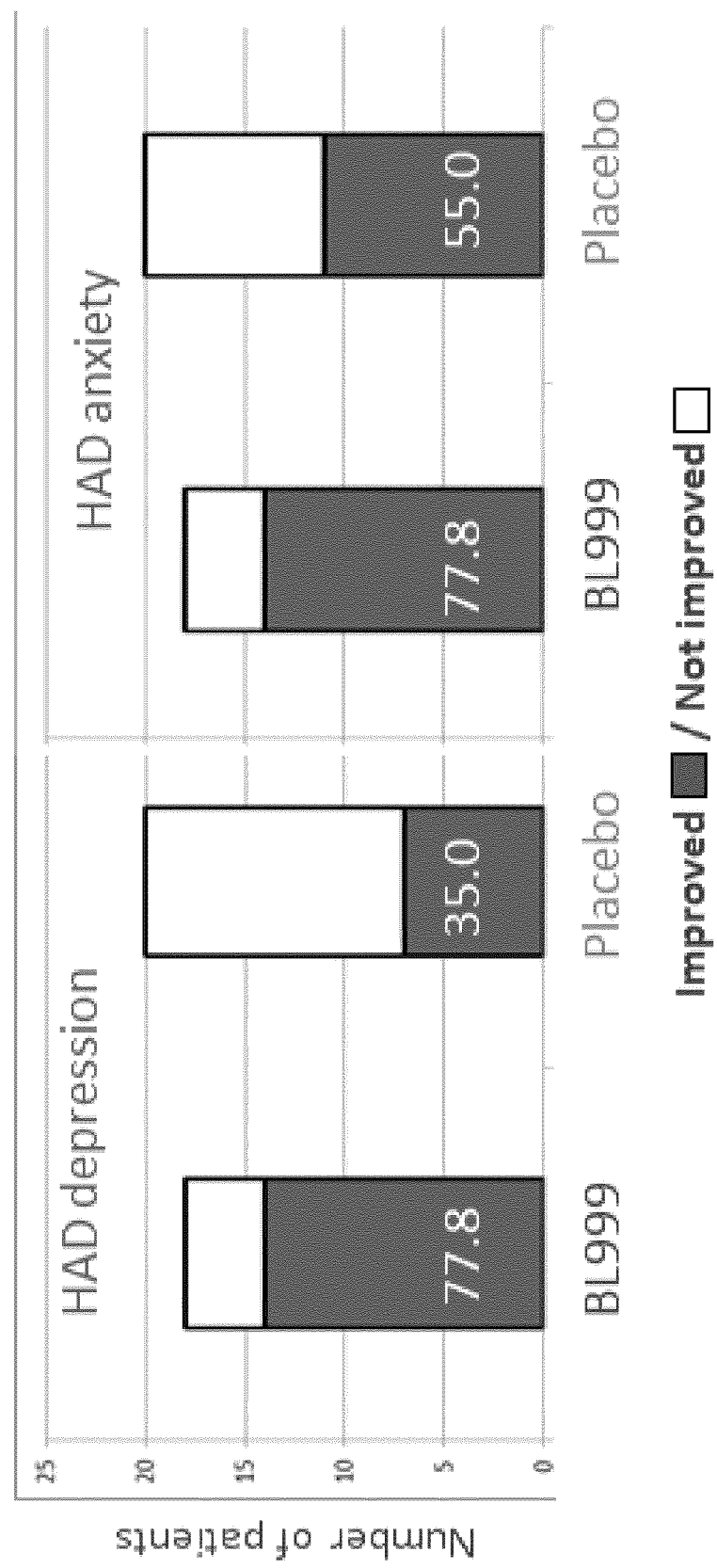
FIG. 2 shows graphs demonstrating the primary outcome from administration of *B. longum* ATCC BAA-999, improvement in depression and anxiety dichomotous scores.

Specifically, FIG. 2 shows that treatment with *B. longum* ATCC BAA-999 improved depression scores both by intention-to-treat analysis (ITT) and per protocol analysis (PP). The beneficial effect of the *B. longum* ATCC BAA-999 was maintained at one month post-treatment (follow-up visit, with both ITT and PP analysis).

FIG. 3 shows that, adjusting for baseline, depression improvement as a continuous variable was achieved in the *B. longum* ATCC BAA-999 group (ANCOVA, p=0.049). This beneficial effect was not maintained at one month post-treatment. Treatment with *B. longum* ATCC BAA-999 did not improve anxiety scores when analyzed as continuous variables.

Figure 4:
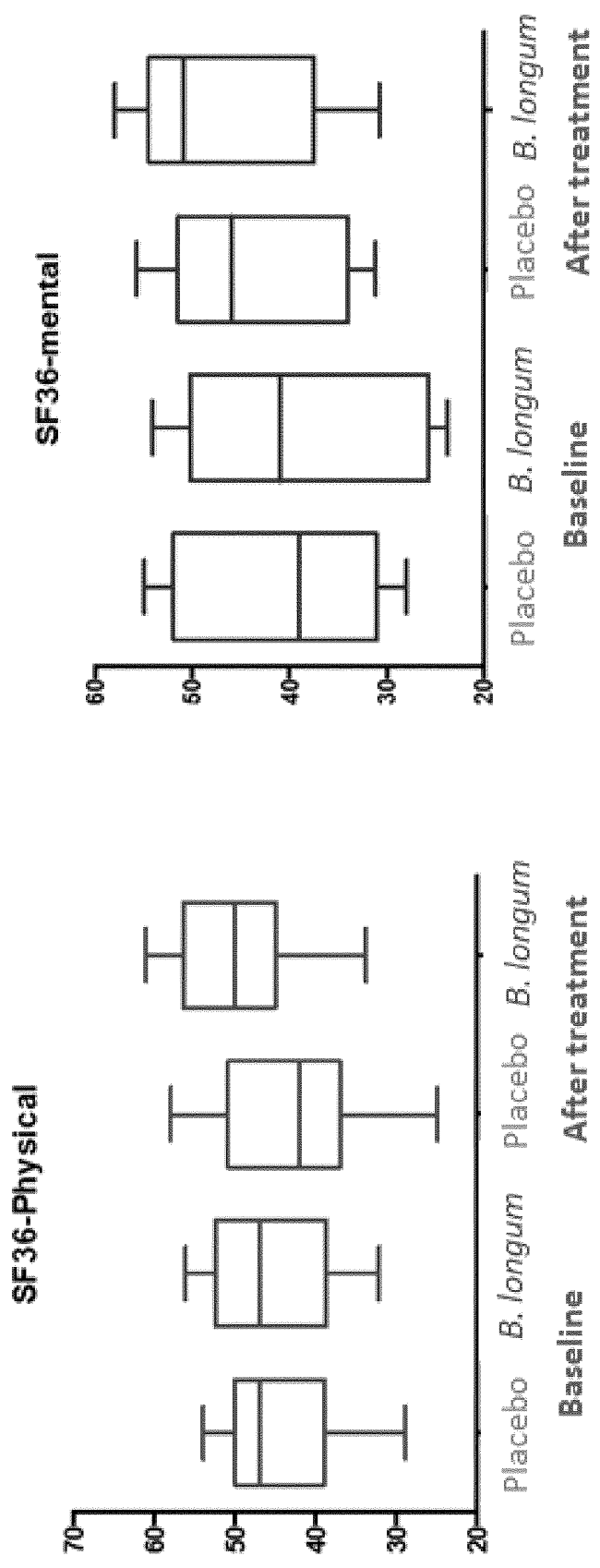

FIGS. 4 and 5 show that there was a statistically significant improvement in SF-36 physical global domain, as well as in general physical health (Physical functioning) and problems with work or other daily activities (Role physical), in the *B. longum* ATCC BAA-999 compared to placebo. Non-significant differences between treatment groups were observed in SF-36 mental global domain. However, when analyzing the mental subdomains, non-statistically significant trends for improvement in Vitality and Role emotional were observed in the *B. longum* ATCC BAA-999 treated group.

Figure 6:
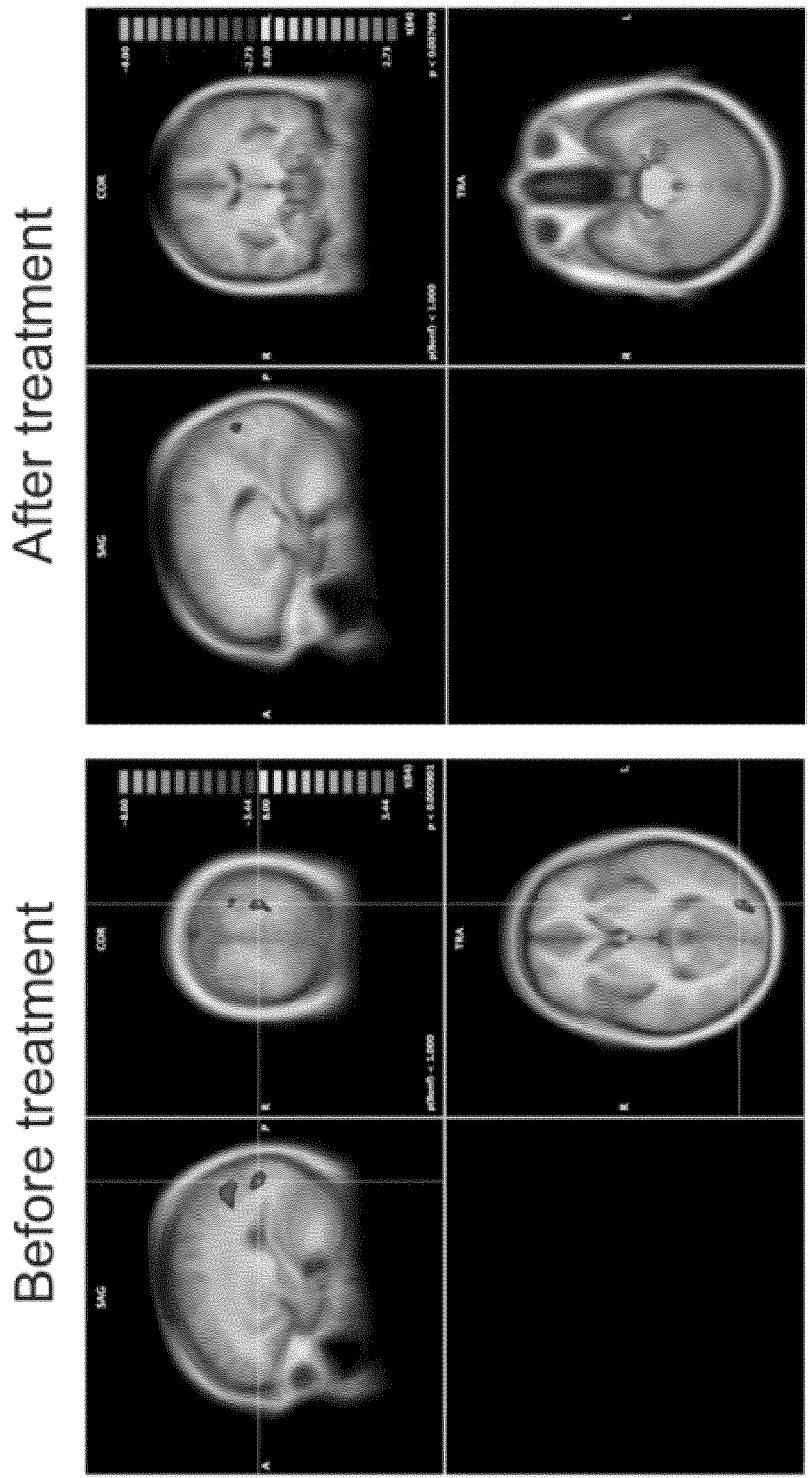
FIG. 6 shows fMRI images demonstrating greater engagement of the visual association and parietal cortices in the group administered *B. longum* ATCC BAA-999 relative to the placebo group and lesser engagement of brain centers involved in emotion and mood (amygdala and fronto-limbic region) in the group administered *B. longum* ATCC BAA-999 relative to the placebo group.

FIG. 6 shows that functional MRI revealed significant reductions from baseline in response to negative emotional stimuli in multiple brain areas involved in emotion processing, including amygdala, frontal and temporal brain regions (p<0.001), in patients treated with *B. longum* ATCC BAA-999 compared with placebo. Specifically, before treatment, there was no major difference in response to fear stimuli vs fixation between placebo and *B. longum* groups, except for greater engagement of the visual association and parietal cortices in *B. longum* group. However, at the end of the treatment, there was greater engagement of the amygdala, frontal, and temporal cortices and reduced engagement of occipital regions in placebo group.

No statistically significant differences were observed in anxiety, cognitive function, inflammatory markers, serum BDNF levels or gut microbiota profiles in patients treated with *B. longum* ATCC BAA-999 compared to placebo.

CONCLUSION

The results demonstrate that a six-week treatment with *B. longum* ATCC BAA-999 improves co-morbid depressive symptoms, overall gastrointestinal symptoms and quality of life in patients with IBS. This effect is associated with changes in the brain activation patterns in the amygdala and fronto—limbic regions, suggesting that reduction in limbic reactivity may underlie the beneficial effect of *B. longum* ATCC BAA-999.

The invention is claimed as follows:

1. A method of supplementing a regimen for treatment of a depressive symptom, the regimen comprises administering to an individual in need thereof a synthetic pharmaceutical compound, and comprising administering an edible composition comprising a therapeutically effective amount or a prophylactically effective amount of *Bifidobacterium longum* ATCC BAA-999 to the individual, wherein the depressive symptom is a secondary condition caused by an underlying medical condition selected from the group consisting of an endocrine disease, a cardiovascular disease, a pulmonary disease, a cancer, an autoimmune disease and combinations thereof, and wherein the combination of the synthetic pharmaceutical compound and the edible composition treats the depressive symptom.

2. The method of claim 1, wherein the underlying medical condition is selected from the group consisting of a thyroid abnormality, a heart attack, a chronic obstructive pulmonary disease and rheumatoid arthritis.

* * * * *